United States Patent [19]

Muro et al.

[11] 4,005,084
[45] Jan. 25, 1977

[54] THIENYLMETHYL PHENOXY MORPHOLINE COMPOUNDS

[75] Inventors: Tomio Muro, Nakatsu; Yasuaki Chihara, Fukuoka; Sogo Fukuzawa, Nakatsu; Kiyoshi Ogawa, Fukuoka; Akira Nakanishi, Nakatsu, all of Japan

[73] Assignee: Yoshitomi Pharmaceutical Industries, Ltd., Osaka, Japan

[22] Filed: July 10, 1975

[21] Appl. No.: 594,913

[52] U.S. Cl. .................. 260/247.1 P; 424/248.51; 260/332.2 R; 260/332.3 R; 260/332.3 H
[51] Int. Cl.² ...................................... C07D 413/12
[58] Field of Search .................. 260/247.1, 247.1 P

[56] References Cited

UNITED STATES PATENTS

| | | | |
|---|---|---|---|
| 3,360,526 | 12/1967 | Minor | 260/247.7 S |
| 3,709,892 | 1/1973 | Leeming et al. | 260/247.7 S |
| 3,712,890 | 1/1973 | Lee | 260/247.7 S |
| 3,714,161 | 1/1973 | Mallion et al. | 260/247.7 S |
| 3,814,750 | 6/1974 | Cross et al. | 260/247.1 |

*Primary Examiner*—Natalie Trousof
*Assistant Examiner*—R. W. Ramsuer
*Attorney, Agent, or Firm*—Sughrue, Rothwell, Mion, Zinn & Macpeak

[57] ABSTRACT

Morpholine compounds of the formula:

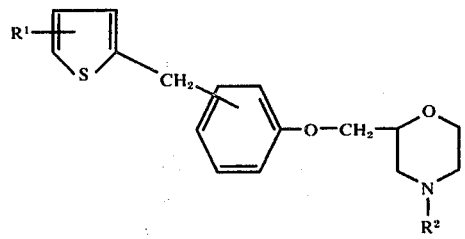

wherein each of $R^1$ and $R^2$ is a hydrogen atom or an alkyl group having 1 to 4 carbon atoms, and pharmaceutically acceptable acid addition salts thereof, have strong inhibitory activities on peptic ulcer, gastric motility and gastric secretion but have very weak acetylcholine antagonistic activity.

5 Claims, No Drawings

THIENYLMETHYL PHENOXY MORPHOLINE COMPOUNDS

This invention relates to novel and therapeutically valuable morpholine compounds of the formula:

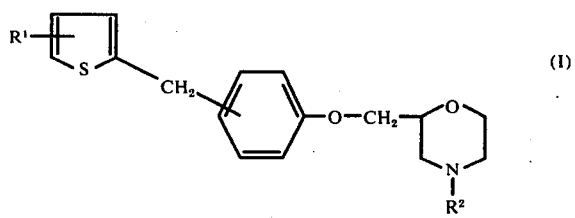

wherein each of $R^1$ and $R^2$ is a hydrogen atom or an alkyl group having 1 to 4 carbon atoms (e.g. methyl, ethyl, propyl or butyl), and pharmaceutically acceptable acid addition salts thereof.

The compounds of formula (I) and pharmaceutically acceptable acid addition salts thereof are strong in inhibitory activities on peptic ulcer, gastric motility and gastric secretion but they are very weak in acetylcholine antagonistic activity.

Anticholinergic agents that are used widely in the medical treatment of various digestive system diseases such as peptic ulcer, gastrointestine spasm or gastric hyperacidity, have undesirable side effects such as dryness of the mouth, blurred vision and other atropine-like effects. Antacids are also used mainly to control gastric acidity. The antacids, on the other hand, have limited effectiveness as they act only to neutralize the acid after it has been secreted into the stomach, and furthermore, have a very short duration of activity. Therefore, it is highly desirable that medicines for the digestive system be available which might take the place of the anticholinergic agents.

As a result of the present inventors' search for such medicines, it has now been found that the compounds of formula (I) and pharmaceutically acceptable acid addition salts thereof have strong inhibitory activities on peptic ulcer, gastric motility and gastric secretion but have very weak acetylcholine antagonistic activity.

The compounds of formula (I) can be produced by one of the following methods (i) to (iv):

Method (i)

By subjecting a compound of the formula:

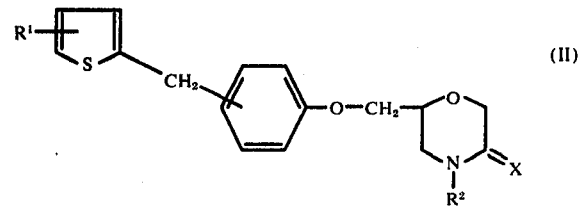

wherein $R^1$ and $R^2$ are as defined above and X is an oxygen atom or a sulfur atom, to reduction with a complex metal hydride such as lithium aluminum hydride, sodium bis(2-methoxyethoxy)aluminum hydride or sodium borohydride.

The reaction is usually carried out in an inert solvent such as an ether (e.g. diethyl ether, tetrahydrofuran or dioxane), an aromatic hydrocarbon (e.g. benzene, toluene or xylene) or an alcohol (e.g. methanol, ethanol, propanol, 2-propanol, butanol or ethylene glycol), at a temperature of from about 35° to 80° C.

Method (ii)

By reacting a compound of the formula:

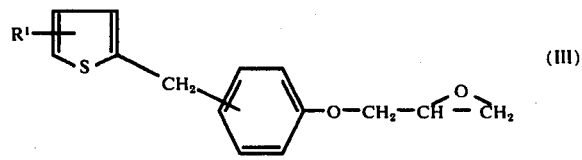

wherein $R^1$ is as defined above, with a compound of the formula:

$$R^2-HNCH_2CH_2-Y \qquad (IV)$$

wherein $R^2$ is as defined above and Y is a reactive atom or group such as a halogen atom (e.g. Cl, Br or I) or —OSO$_2$—OR [R being a hydrogen atom, an alkyl group having 1 to 4 carbon atoms (preferably methyl) or an aryl group (preferably pheny or p-tolyl); preferably a hydrogen atom].

The reaction is usually carried out in a solvent such as water, an alcohol, an ether or an aromatic hydrocarbon or a mixture thereof, in the presence of a basic catalyst (e.g. sodium hydroxide, potassium hydroxide, barium hydroxide, sodium carbonate or potassium carbonate), at a temperature of from room temperature to a boiling point of the solvent used. In this case, when the reaction is carried out under mild conditions such as by the use of a relatively small amount of the basic catalyst at room temperature, the intermediate of the following formula (V) is firstly formed:

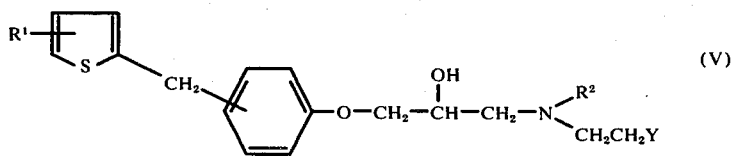

wherein $R^1$, $R^2$ and Y are as defined above. The intermediate of formula (V) can be subjected, with or without isolation and purification, to the next reaction, i.e. ring closure by treating it in the presence of an additional amount of a basic catalyst at an elevated temperature.

Method (iii)

(In case that $R^2$ is a hydrogen atom)
By subjecting a compound of the formula:

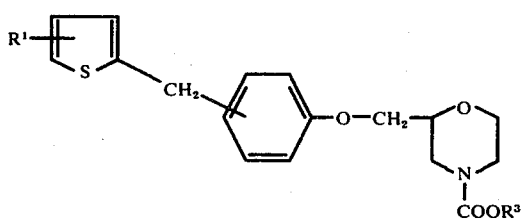

wherein $R^1$ is as defined above and $R^3$ is a benzyl group or an alkyl group having 1 to 4 carbon atoms (e.g. methyl, ethyl, propyl or butyl), to hydrolysis.

The hydrolysis is usually carried out by heating a compound of the formula (VI) in water, methanol, ethanol, or ethylene glycol or amixture thereof in the presence of a conventional catalyst (e.g. sodium hydroxide, potassium hydroxide, barium hydroxide, hydrochloric acid or hydrobromic acid), or by treating it with hydrobromic acid in acetic acid, for about 15 to 45 hours.

Method (iv)

(In case that $R^2$ is an alkyl group having 1 to 4 carbon atoms)
By reacting a compound of the formula:

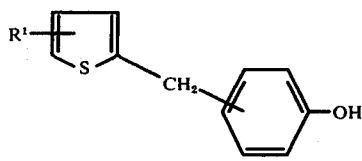

wherein $R^1$ is as defined above, with a compound of the formula:

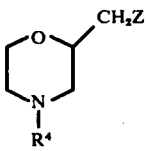

wherein $R^4$ is an alkyl group having 1 to 4 carbon atoms (e.g. methyl, ethyl, propyl or butyl) and Z is a reactive atom or group such as a halogen atom (e.g. Cl, Br or I) or a sulfonyloxy group (e.g. mesyloxy, phenylsulfonyloxy or tolylsulfonyloxy).

The reaction is usually carried out without a solvent or in a solvent such as an alcohol, an ether, an aromatic hydrocarbon, dimethylformamide, dimethylsulfoxide, pyridine or a mixture thereof, in the presence of a basic catalyst (e.g. sodium hydroxide, potassium hydroxide, sodium carbonate, potassium carbonate, sodium ethoxide, potassium tert-butoxide, metallic sodium, sodium amide or sodium hydride), at a temperature of from room temperature to a boiling point of the solvent used.

The starting compounds of formulas (II) and (VI) can be prepared according to the following Scheme I, for example:

Scheme I

-continued

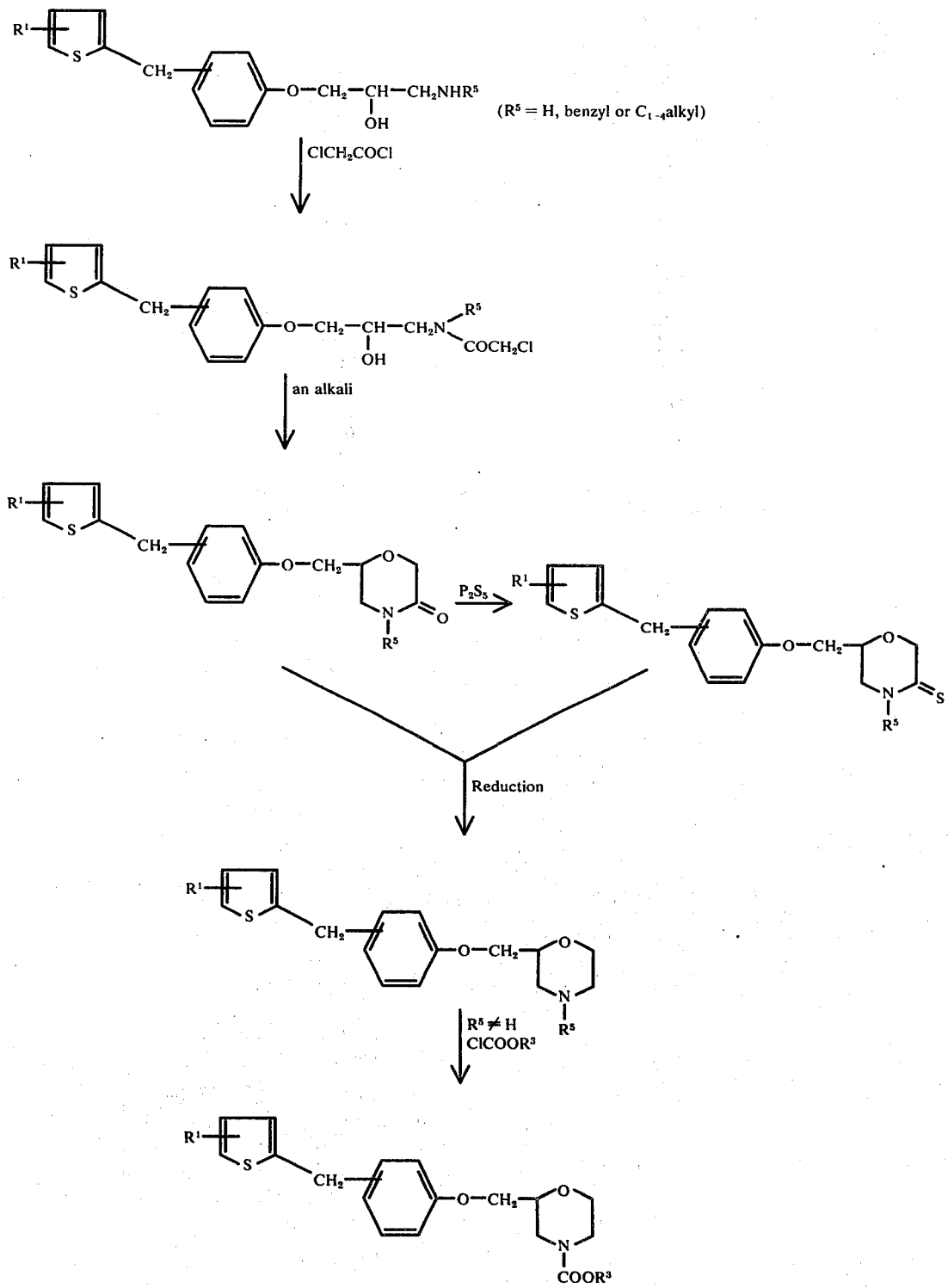

The compounds of formula (I) can be converted into the corresponding acid addition salts in a conventional manner, namely by treating the compound with various inorganic and organic acids, for example, hydrochloric, hydrobromic, sulfulic, fumaric, maleic, oxalic, succinic, malic, o-(p-hydroxybenzoyl)benzoic acid or phenolphthalin.

Since the compounds of formula (I) contain an asymmetric carbon atom, they may be obtained as racemic mixtures or as optical isomers. It is understood that the optical isomers as well as racemic mixtures are embraced within the scope of the present invention.

The compounds of formula (I) and pharmaceutically acceptable acid addition salts thereof are strong in inhibitory activities on peptic ulcer, gastric motility and gastric secretion, but are very weak in acetylcholine antagonistic activity as shown, for example, by following tests.

I. Inhibitory activity on Shay ulcer in rats

Female Wistar rats (140–180 g) were fasted for 44 hours but allowed free access to ater after which the pylorus was ligated as described by Shay et al. in the Gastroenterology, vol. 5, pp 43–61 (1945). Immediately after this ligation, test compound was given subcutaneously. Ten hours later, the animals were sacrificed by an overdose of ether, the stomach was removed and examined for lesions. The logarithm of the sum of each damaged area per rat was referred to as the ulcer index.

The Per Cent Inhibition was calculated as follows:

$$\text{Inhibition (\%)} = \frac{\text{Ulcer index (Control)} - \text{Ulcer index (Test compound)}}{\text{Ulcer index (Control)}} \times 100$$

The $ED_{50}$ was read from the semilogarithmic graph on which the Per Cent Inhibition was plotted vs. mg/kg dose.

II. Inhibitory activity on gastric motility under stress in rats

The procedure described by K. Watanabe in the Chemical & Pharmaceutical Bulletin, vol. 14, pp. 101–107 (1966) was employed.

Male Wistar rats weighing about 250 g were used. After fasting for 18 hours, rats were fixed on their backs by the limbs with thread on boads and immersed into water to the depth of the xiphoid cartilage. Temperature of water was kept at 22° C.

Pressure change in small rubber balloon fixed in the grandular stomach was recorded with pressure transducer (Nihon Koden Kogyo Co., Ltd., MP-4T). The balloon was inserted from the forestomach under light ether anesthesia. Initial pressure was kept at the height of 10 mmHg.

When the effect of anesthesia and of the operation diminished, test compound was administered into the stomach through the polyethylene tube which was previously inserted into the stomach with the balloon.

III. Inhibitory activity on gastric secretion in rats

After fasting for 48 hours, the stomach of male Wistar rats weighing about 200 g were ligated at the pylorus under light ether anesthesia as described by Shay et al. in the Gastroenterology, vol. 5, pp. 43–61 (1945). Immediately after this ligation, test compound was given subcutaneously. Four hours later, the gastric juice in the stomach was collected and centrifuged for each rat and expressed as ml per 100 g of body weight.

The $ED_{50}$ was calculated in the same manner as Test (I) on Shay ulcer.

IV. Acetylcholine antagonistic activity

Acetylcholine antagonistic activity was tested according to the method described by J. M. Van Rossum et al. in the Archives Internationales de Pharmacodynamie et de Therapie, vol. 143, pp. 240–246 and pp. 299–330 (1963). The $pA_2$ is the negative of the logarithm, to the base 10, of the molar concentration of the test compound which reduced the effect of a double dose of acetylcholine on contracting action of the guinea pig intestine compared with that of a single dose.

| Results | Test Compounds | |
|---|---|---|
| | A | Atropine |
| Inhibitory activity on Shay ulcer, $ED_{50}$ mg/kg | 5.5 | 0.5 |
| Inhibitory activity on gastric motility, $ED_{50}$ mg/kg | 2.1 | 3 |
| Inhibitory activity on gastric secretion, $ED_{50}$ mg/kg | 4.5 | 0.12 |
| Acetylcholine antagonistic activity, $pA_2$ | 5.2 | 8.9 |

Compound A is identified below:
A: 2-[2-(2-thenyl)phenoxymethyl]morpholine maleate (compound of the invention)

In view of the tests above, the compounds of formula (I) and pharmaceutically acceptable acid addition salts thereof are strong in inhibitory activities on peptic ulcer, gastric motility and gastric secretion but are very weak in acetylcholine antagonistic activity. It can be said that the compounds of formula (I) and pharmaceutically acceptable acid addition salts thereof are useful as medicines for prophylaxis and treatment of peptic ulcer, chronic gastritis, acute gastritis, gastric hyperacidity and gastrointestinal spasm and for prevention of stress-induced peptic ulcer.

The compounds of formula (I) and pharmaceutically acceptable acid addition salts thereof can be administered safely per se or in the form of a pharmaceutical composition in admixture with a suitable carrier or adjuvant without adversely affecting the patients.

The pharmaceutical composition can take any conventional form such as tablets, capsules, granules or injectable solutions.

The present invention also embraces a pharmaceutical composition containing a compound (I) or a salt thereof in the form of an injectable solution in a physiologically acceptable liquid, or in the form of a composition for oral or parenteral administration together with a physiologically acceptable carrier or diluent.

FORMULATION EXAMPLE

Tablets each containing 10.0 mg of an active ingredient are prepared by the following compositions:

| | |
|---|---|
| Compound (I) | 10.0 mg |
| Lactose | 64.0 mg |
| Starch | 19.4 mg |
| Microcrystalline Cellulose | 20.0 mg |
| Talc | 5.0 mg |
| Methylcellulose | 0.6 mg |
| Magnesium stearate | 1.0 mg |
| | 120.0 mg |

The daily oral dose of compound (I) and a salt thereof for human adults usually ranges from about 3 to 12 tablets, but it may vary depending upon the age, body weight, and/or severity of the conditions to be treated as well as the response to the medication.

The present invention will be better understood from the following examples, but they are not to be construed as limiting the present invention.

EXAMPLE 1

To a solution of 3.8 g of 4-benzyl-2-[2-(2-thenyl)-phenoxymethyl]-morpholine in 30 ml of toluene was added 1.2 g of ethyl chloroformate, and the mixture was heated under reflux for 6 hours. After cooling, the insoluble material was filtered off and the filtrate was concentrated under reduced pressure to give 3.1 g of crude 4-ethoxycarbonyl-2-[2-(2-thenyl)-phenoxymethyl]morpholine as an oil. The oil was dissolved in 40 ml of ethanol, and a solution of 3.2 g of barium hydroxide in 50 ml of water was added, and the mixture was heated under reflux for 8 hours. After cooling, the insoluble material was filtered off, and the filtrate was concentrated under reduced pressure. The remaining oil was extracted with two 70 ml portions of 5% hydrochloric acid, and the combined water layer was made alkaline with sodium hydroxide. The liberated oil was extracted with benzene, and the benzene extract was dried over potassium carbonate. Then the benzene was distilled off to give 1.6 g of 2-[2-(2-thenyl)phenoxymethyl]-morpholine as an oil. A solution of the oil (1.6 g) in 15 ml of isopropyl ether was added to a solution of 0.65 g of maleic acid in 7 ml of ethanol to give 2.1 g of colorless crystals. The crystals were recrystallized from a mixture of methanol and isopropyl ether (1:1) to give 1.5 g of 2-[2-(2-thenyl)phenoxymethyl]morpholine maleate as colorless crystals, melting at 155°–156° C.

The starting compound, 4-benzyl-2-[2-(2-thenyl)-phenoxymethyl]-morpholine can be prepared according to the following steps (1) to (3):

Step (1):

To a mixture of 29 g of 1-benzylamino-2-[2-thenyl)-phenoxy]-2-propanol, 250 ml of chloroform and 12 g of triethylamine was added dropwise a solution of 10.2 g of chloroacetyl chloride in 50 ml of chloroform over 40 minutes with stirring and cooling to 0° to 5° C. Then the resulting mixture was stirred for 3 hours at room temperature. To the reaction mixture was added 100 ml of water, the separated chloroform layer was washed with 5% hydrochloric acid and with water, and then dried over anhydrous magnesium sulfate. The chloroform was distilled off to give 27 g of N-[2-hydroxy-3-[2-(2-thenyl)phenoxy]propyl]-N-benzyl-chloroacetamide as an oil.

Step (2):

A solution of 27 g of N-[2-hydroxy-3-[2-(2-thenyl)-phenoxy]propyl]-N-benzyl-chloroacetamide in 100 ml of methanol was added dropwise to a solution of 2.3 g of metallic sodium in 200 ml of methanol with stirring at room temperature. The resulting mixture was stirred under reflux for 3 hours. Then the methanol was distilled off under reduced pressure, and the residue was extracted with 200 ml of benzene. The benzene layer was washed with water and dried over anhydrous magnesium sulfate, and then the benzene was distilled off to give 26 g of crude product as an oil. The oil was purified by column chromatography using a column of silica gel and chloroform as an eluent. The fractions containing the objective product were concentrated to give 23 g of 4-benzyl-2-[2-(2-thenyl)phenoxymethyl]-morpholin-5-one as colorless crystals, melting at 97°–99° C.

Step (3):

A solution of 23 g of 4-benzyl-2-[2-(2-thenyl)-phenoxymethyl]-morpholin-5-one in 200 ml of benzene was added dropwise to a suspension of 7 g of lithium aluminum hydride in 200 ml of ether with stirring and cooling. The resulting mixture was heated under reflux with stirring for 5 hours. To the mixture was added 10 ml of ethyl acetate, and the whole mixture was stirred for 30 minutes. To the mixture were added water under cooling and then 300 ml of a saturated aqueous Rochelle salt solution, and the resulting mixture was stirred for 30 minutes. The organic layer was collected and dried over anhydrous magnesium sulfate. The solvent was distilled off to give 20 g of 4-benzyl-2-[2-(2-thenyl)phenoxymethyl]morpholine as an oil. The oil was dissolved in ether, and a mixture of 4.8 g of oxalic acid in ether and ethanol was added to the solution to give 23 g of the corresponding oxalate salt as colorless crystals, melting at 179°–181.5° C. The thus-obtained oxalate was converted into the free base, which was used as the starting compound of Example 1.

EXAMPLE 2

A mixture of 19 g of 1-[2-(2-thenyl)phenoxy]-2,3-epoxypropane, 65 g of 2-aminoethyl hydrogen sulfate, 40 g of sodium hydroxide, 350 ml of ethanol and 200 ml of water was heated under reflux with stirring for 23 hours. Most of the ethanol was distilled off, and the residue was extracted with two 400 ml portions of ethyl acetate. The extract was washed with water and dried over anhydrous magnesium sulfate, and the ethyl acetate was distilled off under reduced pressure. To the residue was added a solution of maleic acid in ethanol. The precipitated crystals were purified in the same manner as in Example 1 to give 2-[2-(2-thenyl)phenoxymethyl]morpholine maleate as colorless crystals, melting at 155°–156° C.

EXAMPLE 3

A solution of 22 g of 1-[2-(2-thenyl)phenoxy]-2,3-epoxypropane in 200 ml of ethanol was added to a mixture of 56 g of 2-aminoethyl hydrogen sulfate, 20 g of sodium hydroxide and 20 ml of water with stirring, and the stirring was continued for 4 hours at room temperature. To the mixture containing the intermediate, 2-[3-(2-hydroxy-3-[2-(2-thenyl)phenoxy]-propylamino]-ethyl hydrogen sulfate, was added a solution of 40 g of sodium hydroxide in 40 ml of water, and the resulting mixture was stirred for 18 hours on a water bath. To the reaction mixture were added 500 ml of water and 700 ml of toluene. The toluene layer was washed with water and dried over anhydrous sodium sulfate, and the toluene was distilled off under reduced pressure. The oily residue was treated in the same manner as in Example 1 to give 2-[2-(2-thenyl)phenoxymethyl]morpholine maleate as colorless crystals, melting at 155°–156° C.

Using the procedure set forth in the above examples, but substituting equivalent amounts of the appropriate starting compounds, the following compounds are also produced:

1. 2-[4-(2-thenyl)phenoxymethyl]morpholine fumarate, M.p. 125°–126° C;
2. 4-methyl-2-[2-(2-thenyl)phenoxymethyl]morpholine maleate, M.p. 136°–137° C;
3. 2-[2-(5-methyl-2-thenyl)phenoxymethyl]morpholine;
4. 2-[2-(5-ethyl-2-thenyl)phenoxymethyl]morpholine.

What is claimed is:
1. The compound:
2-[2-(2-thenyl)phenoxymethyl]morpholine.
2. The compound:

2-[4-(2-thenyl)phenoxymethyl]morpholine.
3. The compound:
4-methyl-2-[2-(2-thenyl)phenoxymethyl]morpholine.
4. The compound:
2-[2-(5-methyl-2-thenyl)phenoxymethyl]morpholine.
5. The compound:
2-[2-(5-ethyl-2-thenyl)phenoxymethyl]morpholine.

* * * * *